United States Patent [19]
Taylor et al.

[11] Patent Number: 5,851,222
[45] Date of Patent: Dec. 22, 1998

[54] IMPLANTABLE MEDICAL DEVICE

[75] Inventors: William J. Taylor, Anonka; John D. Wright, Wyoming; Joseph F. Lessar, Coon Rapids; Gary F. LaBree, Forest Lake, all of Minn.

[73] Assignee: Medtronic, Inc., Minneapolis, Minn.

[21] Appl. No.: 23,015

[22] Filed: Feb. 11, 1998

Related U.S. Application Data

[62] Division of Ser. No. 846,772, Apr. 30, 1997.

[51] Int. Cl.$^6$ .................................................. A61N 1/375
[52] U.S. Cl. ................................................................ 607/36
[58] Field of Search ..................................... 607/1, 36, 37

[56] References Cited

U.S. PATENT DOCUMENTS

| | | | |
|---|---|---|---|
| Re. 3,370 | 2/1869 | Byers ................................... | 129/419 R |
| 4,180,700 | 12/1979 | Kraska et al. ................... | 174/152 GM |
| 4,225,262 | 9/1980 | Koop et al. ............................. | 403/272 |
| 4,495,917 | 1/1985 | Byers ................................... | 128/419 R |
| 4,525,766 | 6/1985 | Peterson . | |
| 4,678,868 | 7/1987 | Kraska et al. ................... | 174/152 GM |
| 4,730,389 | 3/1988 | Baudino et al. ......................... | 29/825 |
| 4,816,621 | 3/1989 | Huebner et al. ................ | 174/152 GM |
| 4,874,910 | 10/1989 | McCoy . | |
| 4,940,858 | 7/1990 | Taylor et al ..................... | 174/152 GM |
| 4,951,011 | 8/1990 | Heckaman et al. . | |
| 5,012,807 | 5/1991 | Stutz, Jr. et al. .................... | 128/419 P |
| 5,076,270 | 12/1991 | Stutz, Jr. et al. .................... | 128/419 P |
| 5,103,818 | 4/1992 | Maston et al. ........................ | 128/419 P |
| 5,104,755 | 4/1992 | Taylor et al. ........................... | 429/181 |
| 5,294,241 | 3/1994 | Taylor et al. ........................... | 65/59.31 |
| 5,306,581 | 4/1994 | Taylor et al. ........................... | 429/181 |
| 5,406,444 | 4/1995 | Selfried et al. .......................... | 361/302 |
| 5,434,017 | 7/1995 | Berkowitz et al. ........................ | 429/94 |

OTHER PUBLICATIONS

"Research Into The Mechanics of Centerless Grinding" by W. B. Rowe, published in Precision Engineering, vol. 1, No. 1, pp. 75–84, Apr. 1979.

"Theoretical Analysis of Rounding Effect in Generalized Centerless Grinding" by T. Moriya, A. Kanai and M. Miyashita, presented at the Proceedings of a Symposium Sponsored by the Production Engineering Division of the American Society of Mechanical Engineers; Fall meeting of the Minerals, Metals & Materials Society, Chicago, IL, Oct. 206, 1994.

"Grit, Glue—Technology Too" Modern Machine Shop, vol. 67, No. 7, pp. 50–60, Dec. 1994.

"Development of Hermetic Microminiature Connectors", by Neilsen et al, presented at the Winter Annual Meeting, Dallas, TX, Nov. 25–30, 1990 of the American Society of Mechanical Engineers.

Primary Examiner—William E. Kamm
Attorney, Agent, or Firm—Thomas F. Woods; Harold P. Patton

[57] ABSTRACT

The present invention relates to centerless grinding methods and corresponding devices such as feedthroughs for implantable medical devices and for batteries for implantable medical devices. The present invention provides certain advantages, including the elimination of longitudinal anomalies in drawn wire and increasing the reliability of implantable medical devices. In a method of the present invention, the surface of an over-size medical grade wire having a known anomaly depth is centerless ground to a depth past which those anomalies disappear. Centerless grinding of the present invention may be accomplished using an abrasive wheel and suitable coolant.

6 Claims, 10 Drawing Sheets

PRIOR ART

IMPLANTABLE MEDICAL DEVICE

This application is a divisional of application Ser. No. 08/846,772 filed Apr. 30, 1997.

FIELD OF THE INVENTION

The present invention relates to a method of removing longitudinal anomalies from feedthrough pins for hermetically sealed implantable medical devices using a centerless grinding technique, and the devices made by such a method.

BACKGROUND OF THE INVENTION

There are numerous applications where it is necessary to penetrate a sealed container with one or more electrical leads so as to provide electrical access to and from electrical components enclosed within. One such application for which the present invention has particular but not limited utility is in body implantable pulse generators (e.g., for the treatment of bradycardia, tachycardia or nerve stimulation), referred to generally herein as implantable pulse generators (IPG's). Typical devices of this type are formed of a metal container housing the electrical power source components of the IPG with a lid or the like welded to the container to close the device and provide it with a hermetic seal.

An electrical lead or pin is electrically connected to the IPG by means of attachment to one or more feedthroughs which penetrate the container but maintain the hermetically sealed environment thereof. A typical feedthrough consists of an external metal part, or frame or ferrule, into which an insulator solid part typically formed of glass, ceramic, or glass and ceramic is sealed. Within the insulator, one or more metal leads or pins are sealed. Since the reliability of critical implantable medical devices depend on hermetic sealing of various components, the integrity of such seals is of paramount importance.

In many implantable devices, metals which have long term corrosion resistance and biocompatability are needed to provide years of reliable service since maintenance or repair possibilities for the devices are extremely limited. Moreover, since such devices are sometimes lifesaving for the patient, failures of the hermetic seal materials can have catastrophic consequences.

Wire fabricated by drawing or forming processes often contains anomalies such as drawlines, cracks or seams. See FIG. 1, where an example of a prior art drawn wire having defects such as cracks and longitudinal seams is shown.

It is a common practice to incorporate wire as conductors in glass-to-metal and ceramic-to-metal seals. The wire anomalies described above can induce the loss of hermeticity in such seals if the orientation of such anomalies is parallel to the seal cross-section. Deep or narrow anomalies in wire are difficult to completely fill with either glass or solder-braze alloys that typically form the types of hermetic seals described above. Deep or narrow anomalies may also act as stress-risers, such that application of thermal or mechanical loads to the seal can induce latent hermetic failure.

The inability of manufactures to routinely produce wire free from the anomalies described above makes it difficult to produce reliable hermetic seals. The inability of wire manufacturers to consistently meet the surface requirements for hermetic seal applications conflicts directly with the opposing requirement for highly reliability components in implantable medical devices.

Other disclosures relating to feedthroughs generally include the U.S. Patents listed below in Table 1.

TABLE 1

Prior Art Patents

| U.S. Pat. No. | Title |
|---|---|
| 4,180,700 | Alloy Composition and Brazing Therewith, Particularly for Ceramic-Metal Seals in Electrical Feedthroughs |
| 4,225,262 | Niobium Coatings for Joining Ceramic to Metal |
| 4,495,917 | Surgically Implantable Disconnect Device |
| 4,525,766 | Method and Apparatus for Forming Hermetically Sealed Electrical Feedthroughs |
| 4,678,868 | Hermetic Electrical Feedthrough |
| 4,730,389 | Method for Fabrication of an Implantable Hermetic Transparent Container |
| 4,816,621 | Ceramic-Metal Feedthrough Lead Assembly and Method for Making Same |
| 4,874,910 | High Lead Density Vacuum Feedthrough |
| 4,940, 858 | Implantable Pulse Generator Feedthrough |
| 4,951,011 | Impedance Matched Plug-In Package for High Speed Microwave Integrated Circuits |
| 4,991,582 | Hermetically Sealed Ceramic and Metal Package for Electronic Devices Implantable in Living Bodies |
| 5,012,807 | Multi-Part Molded Pacemaker Connector and Method of Making Same |
| 5,076,270 | Apparatus and Method for Making Electrical Connections in an Implantable Pacemaker |
| 5,103,818 | System and Method for Completing Electrical Connections in an Implantable Medical Device |
| 5,104,755 | Glass-Metal Seals |
| 5,294,241 | Method for Making Glass to Metal Seals |
| 5,306,581 | Battery with Weldable Feedthrough |
| 5,406,444 | Coated tantalum Feedthrough Pin |
| 5,434,017 | Isolated Connection for an Electrochemical Cell |
| Re. 33,170 | Surgically Implantable Disconnect Device |

As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the teachings of the present invention.

SUMMARY OF THE INVENTION

The present invention has the object of providing solutions to at least some of the foregoing problems existing in the prior art.

The present invention provides certain advantages, including: (a) eliminating longitudinal anomalies in drawn wire; (b) imparting a predictable, uniform finish to the surface of drawn wire; (c) reducing manufacturing costs by reducing substantially the scrap rates for feedthroughs not meeting hermeticity specifications; (d) increasing the degree of hermeticity of implantable medical devices; (e) increasing the reliability of implantable medical devices by abrasive wheel centerless-grinding, and (f) permitting feedthrough dimensions to be more tightly controlled than has heretofore been possible.

The present invention has certain features, including: (a) providing an over-sized medical grade wire having a known anomaly depth, and centerless grinding the surface of the wire to a depth past which those anomalies disappear; (b) centerless grinding of the surface of medical grade wire to a desired diameter and tolerance; (c) centerless grinding of the surface of medical grade wire using an abrasive wheel and suitable coolant; (d) centerless grinding of the surface of medical grade wire by locating the wire work piece using a regulating wheel and appropriately controlling work piece speed during the grinding step; (e) centerless ground feedthroughs in implantable medical devices; (f) centerless ground wire in combination with various hermetic seals in implantable medical devices; (g) centerless ground wire in combination with an implantable medical device having a lithium battery disposed therewithin; (h) centerless ground wire in combination with ceramic hybrid packages or aluminum electrolytic capacitors.

DETAILED DESCRIPTION OF THE PREFERRED EMBODIMENTS

Centerless grinding methods are described in several printed publications, including the first three of the following references: (a) "Research Into the Mechanics of Centerless Grinding" by W.B. Rowe, published in *Precision Engineering*, Volume 1, Number 1, pp. 75–84, April 1979; (b) "Theoretical Analysis of Rounding Effect in Generalized Centerless Grinding" by T. Moriya, A. Kanai, and M. Miyashita, presented at the Proceedings of a Symposium Sponsored by the Production Engineering Division of the American Society of Mechanical Engineers; Fall Meeting of the Minerals, Metals & Materials Society, Chicago, Ill., Oct. 2–6, 1994; (c) "Grit, Glue—Technology Too!," *Modern Machine Shop*, Volume 67, Number 7, pp. 50–60, December 1994, and (d) "Development of Hermetic Microminiature Connectors" by Neilsen et al., presented at the Winter Annual Meeting, Dallas, Tex., Nov. 25–30, 1990 of the American Society of Mechanical Engineers.

Figure 1:
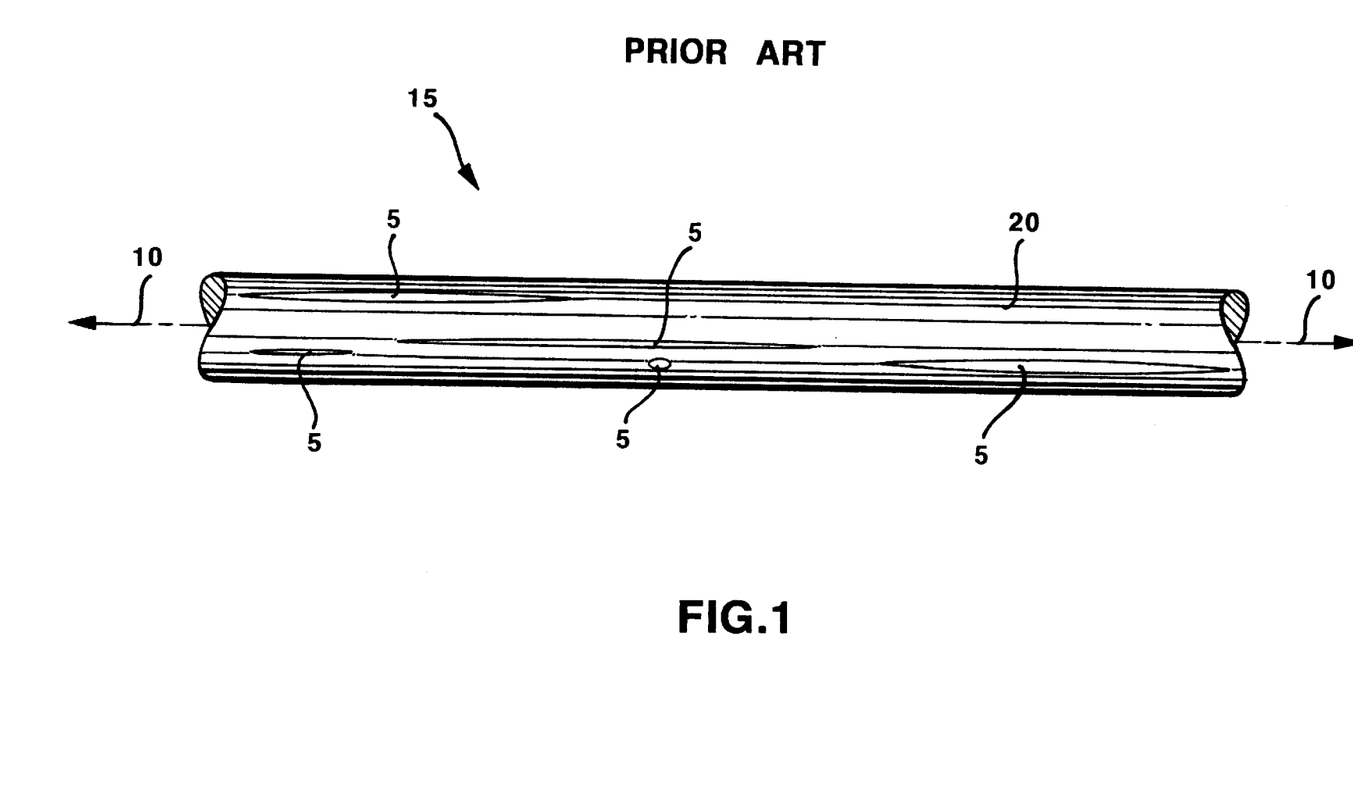
FIG. 1 illustrates a prior art medical grade drawn wire having typical surface defects and anomalies thereon.

FIG. 1 illustrates a prior art medical grade drawn wire 15 having typical defects and anomalies 5 disposed on surface 20 thereof. Defects 5 typically assume the shape of cracks or seams oriented parallel to the central longitudinal axis 10 of wire 15, and formed on the surface thereof. Those seams or cracks 5 typically extend varying depths below surface 20 of wire 15, and may lead to or cause a loss of hermeticity in an implantable medical device or battery containing feedthroughs having pins formed from such drawn wire. Defects 5 may assume shapes or configurations other than longitudinally-oriented cracks or seams such as pits, cracks, fissures and the like.

Figure 2:
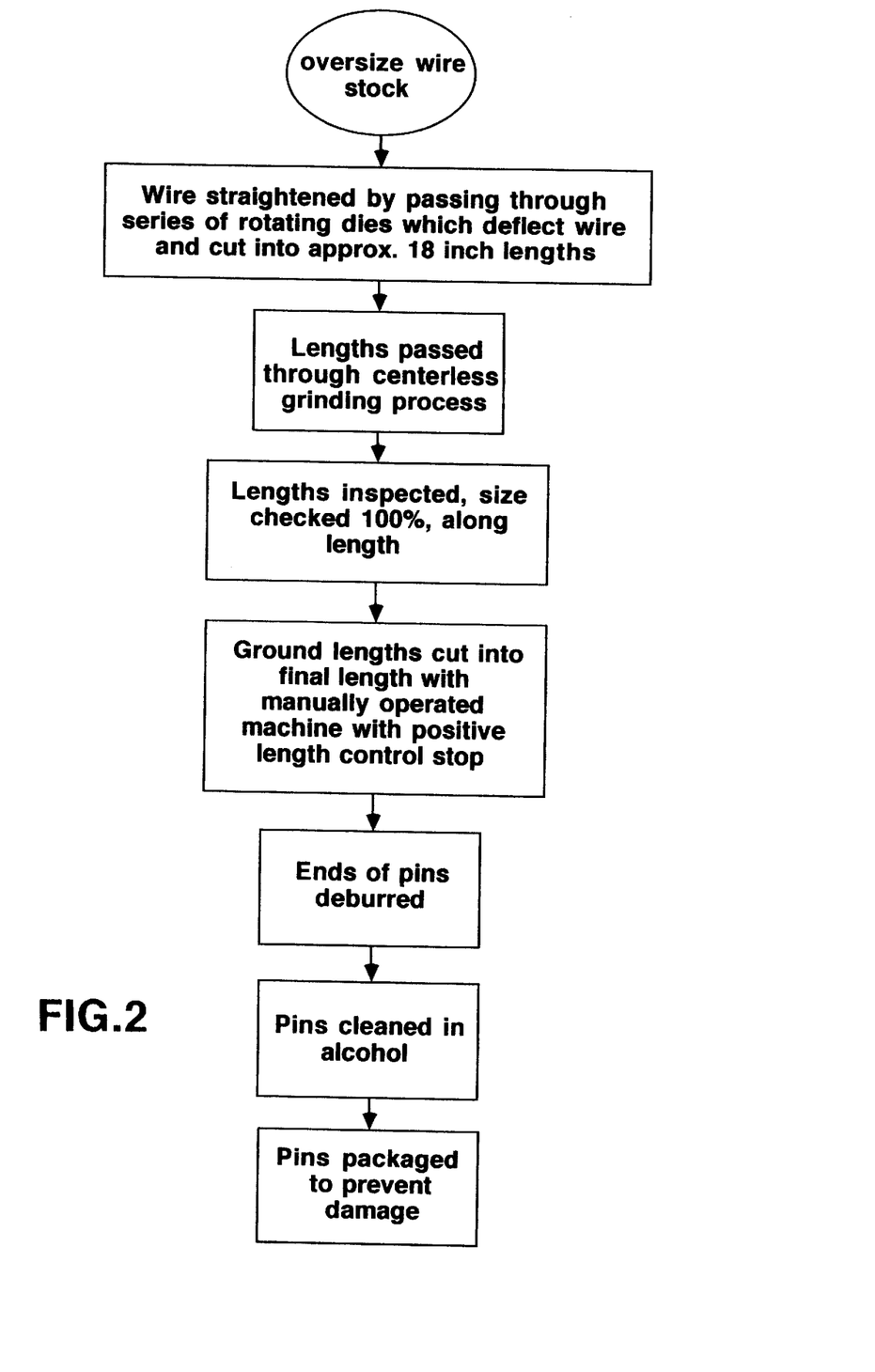
FIG. 2 shows a flow chart of the centerless grinding process of the present invention.

FIG. 2 shows a flow chart of one embodiment of the centerless grinding method of the present invention. In FIG. 2, the method of making a pin for a feedthrough in an implantable medical device comprises the steps of selecting over-size medical grade wire 15 stock, straightening wire 15 by passing the wire through at least one rotating die, cutting the wire to form wire 15 of desired length, centerless grinding wire 15 of desired length to at least substantially remove anomalies or defects 5 from surface 20 thereof, cutting wire 15 to form a feedthrough pin 25 having a final length and two ends, and deburring the ends. After deburring, pin 25 may be cleaned in alcohol and then packaged to prevent damage thereto.

The method of the present invention may further comprise the steps of providing an abrasive wheel for the centerless grinding step, providing a suitable coolant for cooling the abrasive wheel during the centerless grinding step; providing at least one of an aluminum oxide abrasive wheel, cerium oxide abrasive wheel, boron nitride abrasive wheel, silicon carbide abrasive wheel, and diamond abrasive wheel for the centerless grinding step, and providing one of platinum wire, stainless steel wire, aluminum wire, aluminum alloy wire, tantalum wire, niobium wire and titanium wire, and wires formed of alloys, mixtures or combinations thereof, during the selecting step.

The method of the present invention most preferably includes the step of selecting over-size medical grade drawn wire 15 having anomalies or defects 5 which extend a certain know depth beneath surface 20. In the centerless grinding step of the present invention, surface 20 of wire 15 is ground to a depth slightly greater than the known anomaly or defect depth. Most preferably, surface 20 of wire 15 is ground to a depth corresponding to a desired diameter and tolerance.

The method of the present invention is most preferably accomplished using an abrasive wheel or wheels in conjunction with a suitable coolant, as for example employed by JER-NEEN MANUFACTURING COMPANY, INC., of Forest Lake, Minn. Abrasive wheels suitable for the centerless grinding step of the present invention include, but are not limited to, aluminum oxide, cerium oxide, boron nitride, silicon carbide and diamond wheels, and wheels having combinations of the foregoing materials. Coolants should be chosen for the appropriateness of their use with specific wire materials. For example, soft metals such as tantalum and niobium are most suitably ground using a cutting fluid known as HALOCARBON 1.8,® CAS No. 9002-83-9 during the centerless grinding step.

Figure 3:
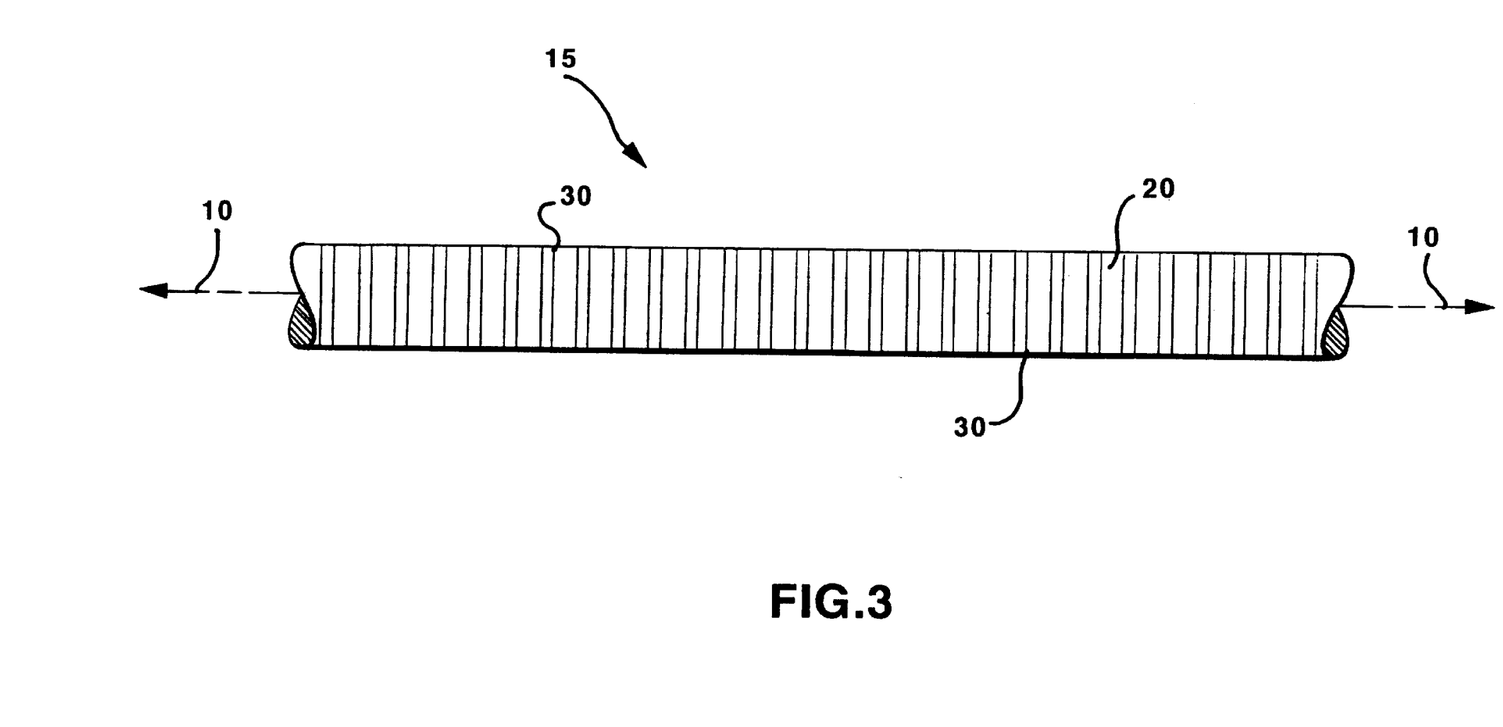
FIG. 3 shows the transverse orientation of tool marks imparted to the surface of centerless ground wire of the present invention.

FIG. 3 shows tool marks 30 on wire 15. Such marks 30 generally have an orientation transverse or substantially transverse to longitudinal axis 10, and are typical of the marks formed on surface 20 of wire 15 during a centerless grinding step of the present invention. The centerless grinding step removes longitudinal anomalies, cracks, seams, pits, scars, fissures and other defects 5 from surface 20 of wire 15 through appropriate centerless application of a spinning abrasive wheel to the surface thereof. Additionally, the centerless grinding step has been discovered to impart a predictable and uniform finish to surface 20 of wire 15.

The present invention is directed especially to centerless ground pins 25 in feedthroughs for lithium batteries for implantable medical devices, implantable pulse generators and defibrillators, implantable neurological stimulators, ceramic hybrid packages and aluminum electrolytic capacitors. The reliability of hermetic seals utilized in such devices has been discovered to be enhanced substantially by centerless ground wire 15. This is because anomalies 30 induced in wire 15 by centerless grinding are generally oriented transverse or substantially transverse to longitudinal wire axis 10, thereby redistributing interfacial stresses in a direction away from axis 10. Such redistribution of interfacial stresses has been discovered to eliminate potential pathways for helium leaks that often characterize prior art, conventional drawn wire.

Centerless grinding and the abrasive wheels utilized therein, are described in detail in the foregoing Modern Machine Shop, Rowe and Moriya papers, as well as in other printed publications known to those skilled in the art.

Controlled removal of material from the surface of wire 15 by centerless grinding is generally accomplished as follows. First, the work piece or wire is positioned using a regulating wheel, typically rubber-bonded, which sets the wire a slight predetermined angle to an abrasive grinding wheel. The regulating wheel controls the speed at which the wire rotates during the centerless grinding process, and brings the wire into a grinding position rapidly. The wire finds its own center as it is rotated between the regulating wheel and the abrasive grinding wheel. Out-of-round material on the wire is pushed into the grinding wheel and ground away. The wire rests on a blade located between the abrasive grinding and regulating wheels, forcing what remains into the grinding wheel at the next rotation.

A preferred centerless grinding machine for use in the method of the present invention is a DEDTRU centerless grinder, model no. 6/12, manufactured by UNISON CORPORATION® of Ferndale, Mich. A preferred centerless grinding abrasive wheel for use in the method of the present invention is a cubic boron wheel, model no. BN180 manufactured by SUPERABRASIVES, INC. of Ferndale, Mich. A preferred feed speed for the centerless grinding method of the present invention no more than 2–3 feet per minute, with an abrasive or grinding wheel speed of about 3,500 RPM. It is preferred that a spring-tempered steel blade be attached to top portion of the regulating wheel to support the wire as it is being ground by the abrasive wheel. Additionally, it is highly preferred that stock cooling equipment not be employed in the centerless grinding method of the present invention, and that a custom misting apparatus be configured to spray a mist onto the abrasive wheel during the centerless grinding process as the wire is being feed past the wheel.

The method and apparatus of the present invention include glass-to-metal feedthroughs having centerless ground pins disposed therewithin, ceramic-to-metal feedthroughs having centerless ground pins disposed therewithin; glass/ceramic-to metal feedthroughs having centerless ground pins disposed therewithin; glass-to-ceramic feedthroughs having centerless ground pins disposed therewithin; hermetic feedthroughs in implantable pulse generators and defibrillators having centerless ground pins disposed within the feedthroughs thereof; hermetic feedthroughs in implantable power sources such as batteries and electrochemical cells having centerless ground pins disposed within the feedthroughs thereof; hermetic feedthroughs in aluminum electrolytic capacitors having centerless ground pins disposed in the feedthroughs thereof; hermetic feedthroughs in ceramic hybrids having centerless ground pins disposed in the feedthroughs thereof, and corresponding methods of making and using same.

Figure 4:
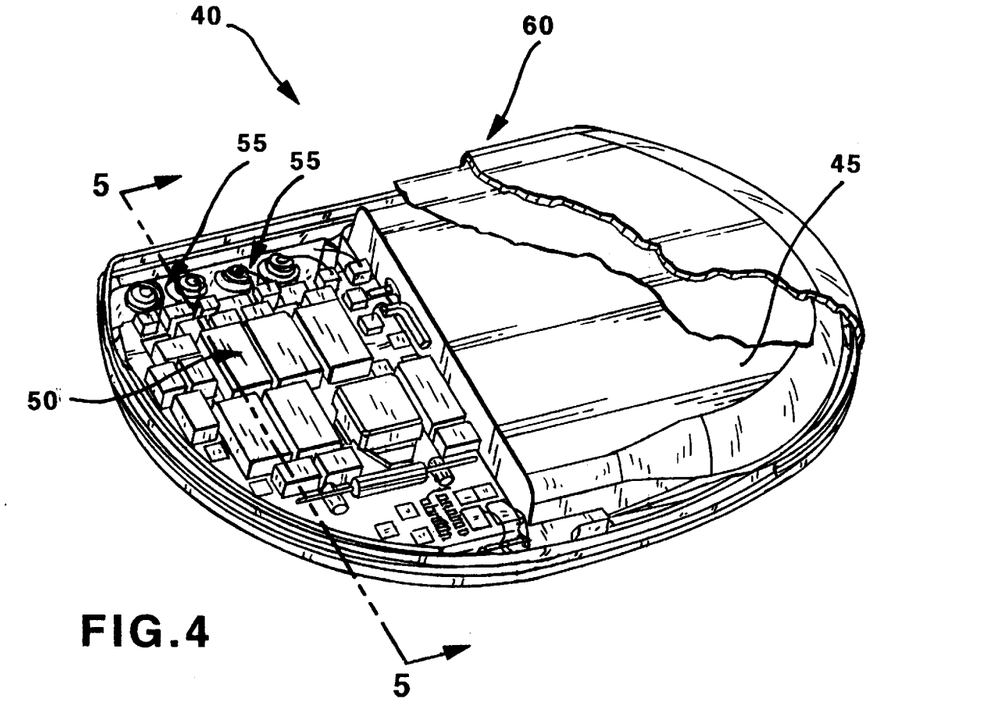
FIG. 4 shows a perspective, cut-away view of the internal components of an implantable medical device of the present invention.
Figure 5:
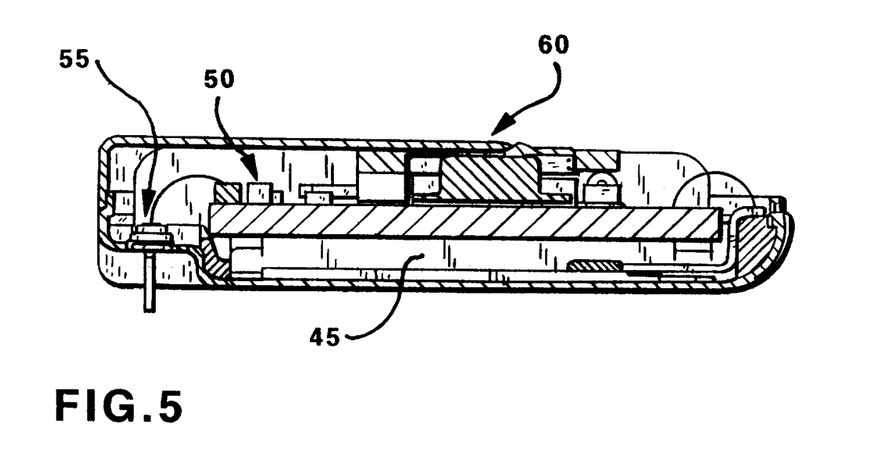
FIG. 5 shows a cross-section view of the implantable medical device of FIG. 4.

FIG. 4 shows a perspective, cut-away view of the internal components of an implantable medical device of the present invention. In FIG. 4, a generic implantable pulse generator (or IPG) IPG 40 is shown. IPG 40 includes battery section 45, hybrid electronics section 50, and a collection of feedthroughs 55, all enclosed by can, shield or container 60. Conductor materials for feedthroughs 55 are selected based upon their reported stability in contact with body fluids. Centerless ground feedthrough pins 25 for this application may be formed from, for example, tantalum, niobium, titanium and platinum, and alloys, combinations and mixtures thereof. Such pins 25 may be incorporated in, for example, hermetic feedthroughs utilizing ceramic-to-metal, glass-to-metal, and ceramic/glass-to-metal sealing technology. FIG. 5 shows a cross-section view of the implantable medical device of FIG. 4.

Figure 6:
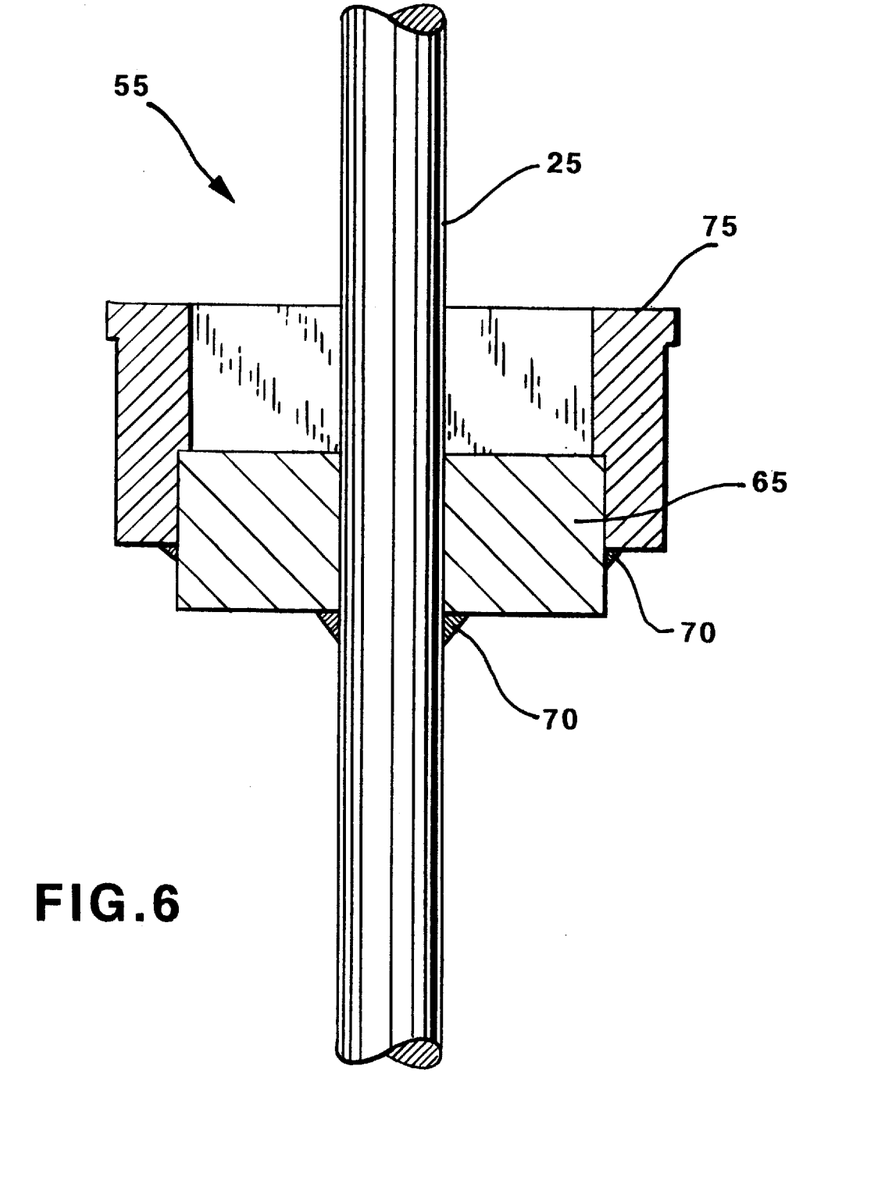
FIG. 6 shows a cross-sectional view of one embodiment of a ceramic-to-metal feedthrough of the present invention.

FIG. 6 shows a cross-sectional view of one embodiment of a single-pin ceramic-to-metal feedthrough 55 of the present invention. The present invention includes within its scope, however, .feedthroughs 55 having multiple centerless ground pins 25 disposed therein. Sealing of feedthrough 55 most preferably occurs in a vacuum furnace, where metallized aluminum oxide insulator 65 is joined by gold braze 70 to centerless ground pin 25 and surrounding metal body or cylinder 75. Centerless ground pin 25 is most preferably formed of tantalum, niobium or platinum, or alloys thereof. Outer body, cylinder or ferrule 75 is most preferably formed of a metal suitable for welding to titanium, from which shield 60 of FIGS. 4 and 5 is typically formed. Gold braze 70 joins insulator 65 to electrically conductive pin 25 and outer body 75.

Figure 7:
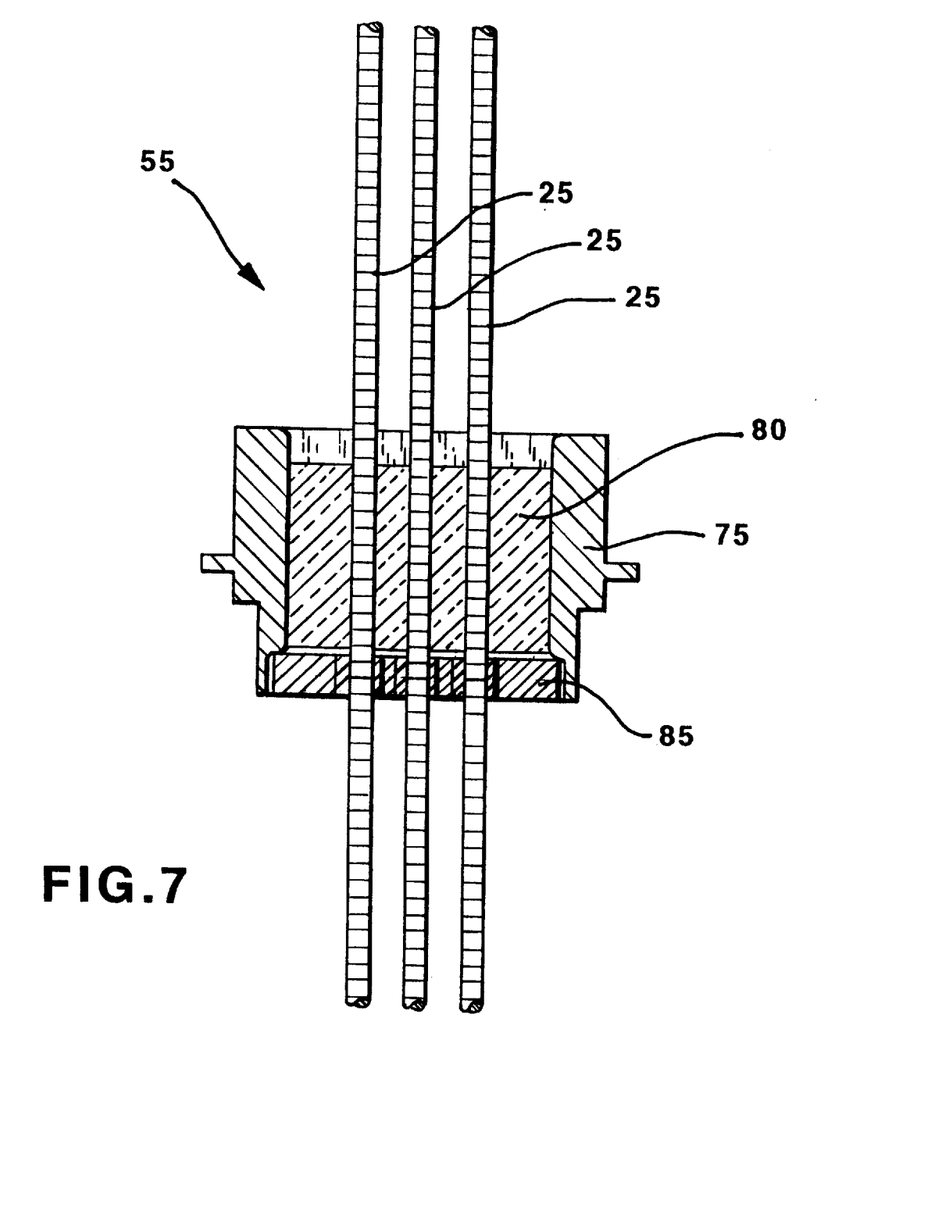
FIG. 7 shows a cross-sectional view of one embodiment of a multi-pin glass-to-metal feedthrough of the present invention.

FIG. 7 shows a cross-sectional view of one embodiment of a multi-pin glass-to-metal feedthrough of the present invention. A plurality of centerless ground pins 25 is shown in FIG. 7. Pins 25 are most preferably formed of tantalum, niobium, titanium or platinum, or alloys thereof. Pins 25 are sealingly engaged and sealing surrounded by sealing glass 80, which is selected to match the thermal expansion characteristics of the metal or metals from which centerless ground pins 25 are formed. Ferrule, metal body or cylinder 75 sealingly surrounds and engages glass 80, and is most preferably formed of a metal suitable for brazing or welding to a metal such as titanium, from which container 60 is typically formed.

In FIG. 7, high temperature barrier glass or barrier ceramic 85 sealingly engages sealing glass 80 and is selected to be compatible with the thermal expansion characteristics of sealing glass 80. One purpose of glass or ceramic barrier 85 is to prevent contact of sealing glass 80 with fixture material such as graphite during the sealing operation. Metal vapor deposits on such fixtures may result in a chemical reaction and bond with glass 80, which is undesirable.

Figure 8:
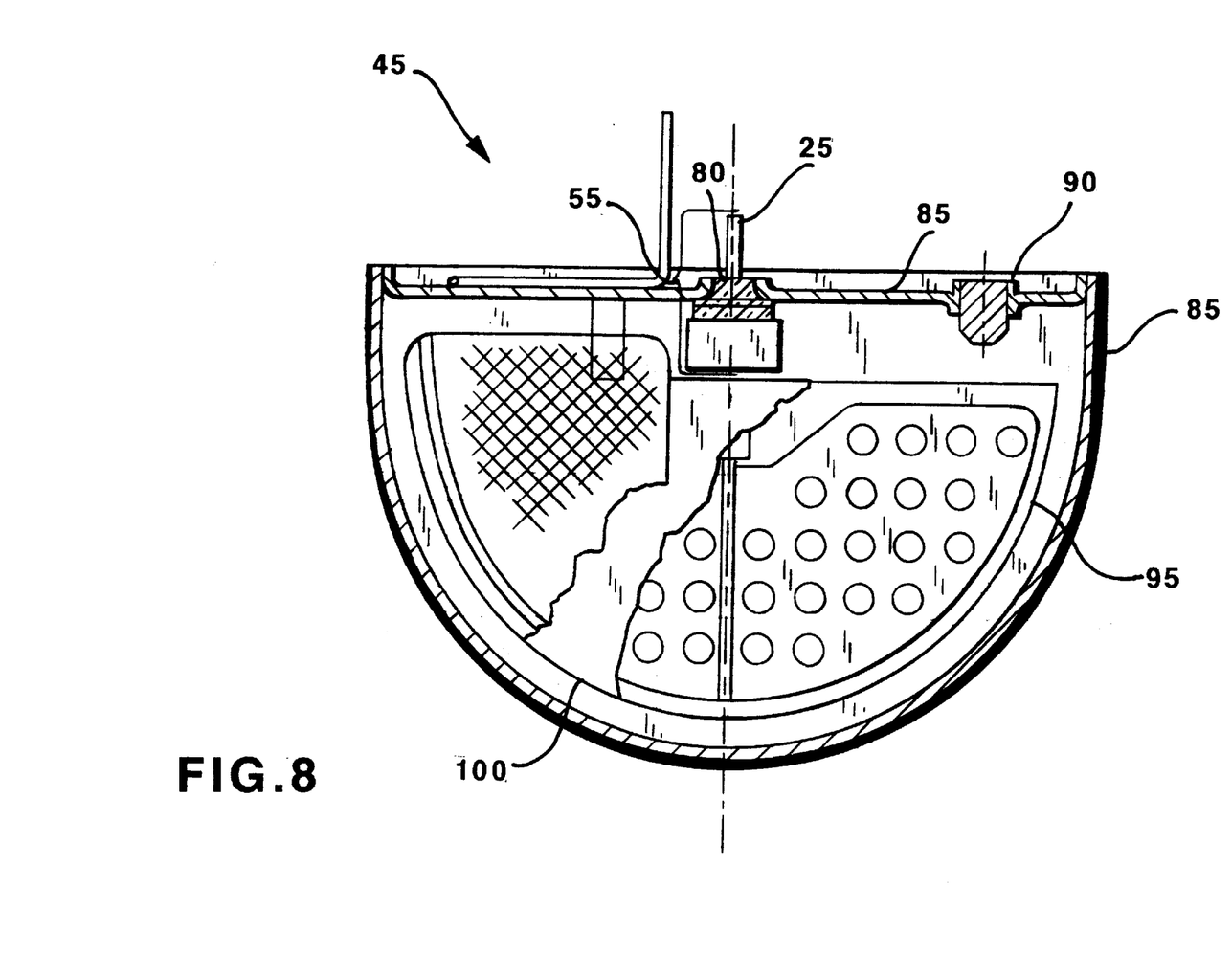
FIG. 8 shows a cross-sectional view of one embodiment of a battery feedthrough of the present invention and the corresponding battery for an implantable medical device.

FIG. 8 shows a cross-sectional view of one embodiment of a battery feedthrough 55 of the present invention and corresponding power source 45 for an implantable medical device 40. Generic power source 45 may be an electrochemical cell, electrolytic capacitor, or battery in an implantable medical device 40. Centerless ground pin 25 is most preferably formed of molybdenum, tantalum, niobium, titanium or platinum, or alloys thereof.

Other suitable metals for forming pin 25, depending on the particular application at hand and the type of feedthrough desired (i.e., pacemaker feedthroughs, battery feedthroughs, ceramic hybrid assembly feedthroughs, capacitor feedthroughs, electrolytic aluminum capacitor feedthroughs, and the like), include platinum, aluminum, aluminum alloys, stainless steel, 400-series stainless steel such as 446 stainless steel (especially useful in respect of battery feedthrough applications), and 300-series stainless steel such as 304L stainless steel (especially useful in respect of battery feedthrough applications).

Referring to FIG. 7 again, pin or electrical lead wire 25 may be electrically connected to the cathode or anode the battery 45. Sealing glass 80 in feedthrough 55 is preferably selected to be compatible with the thermal expansion characteristics of centerless ground pin 25 and the typically corrosive environment of the battery. For example, lithium resistant glasses known to those skilled in the art such as TA-23, Cabal-12 or other suitably resistant glasses, are positioned around a portion of pin 25 in sealing engagement with pin 25. Battery cover 85 is most preferably formed of "superalloys" such as MP35N, stainless steels such as 304L and 316L, or titanium and its alloys.

Feedthrough ferrule 75 is preferably formed of a material similar to that employed to form battery case 85. Ferrule 75 surrounds and sealingly engages glass 80. Electrolyte fill port 90 is employed to fill battery 45 with an appropriate is amount of electrolyte fluid. Fill port 90 includes a plug for sealing battery 45 once such an amount of electrolyte has been added thereto. Anode or cathode material is disposed within battery case 85. The anode and cathode are separated by an ionically permeable separator 100.

Battery 45 of FIG. 8 most preferably has a lithium anode and an electrolyte comprising a lithium salt in an organic solvent. The lithium salt is preferably $LiClO_4$, lithium trifluorosulfonate, $LiPF_6$, $LiCF_3SO_3$, $LiBF_4$, or $LiAsF_6$. The organic solvent is preferably propylene carbonate, glyme, diglyme, dioxolane, dimethyl sulfoxide, sulfolane, gamma butyrolactone and various mixtures thereof. The cathode material is preferably manganese dioxide, silver vanadium oxide ($Ag_2V_4O_{11}$), vanadium oxide ($V_6O_{13}$), carbon monofluoride ($Cf_x$) and various mixtures thereof. The anode, cathode and electrolyte components of battery 45 are enclosed in case 85, the case preferably hermetically sealing the components to prevent discharge of harmful gases and liquids so that the battery may be suitable for use in applications where sealing is critical such as in implantable medical devices. A hermetic seal provides an insulated electrical connection from the case interior to the case exterior and preferably also maintains the hermetic seal of the case.

Figure 9:
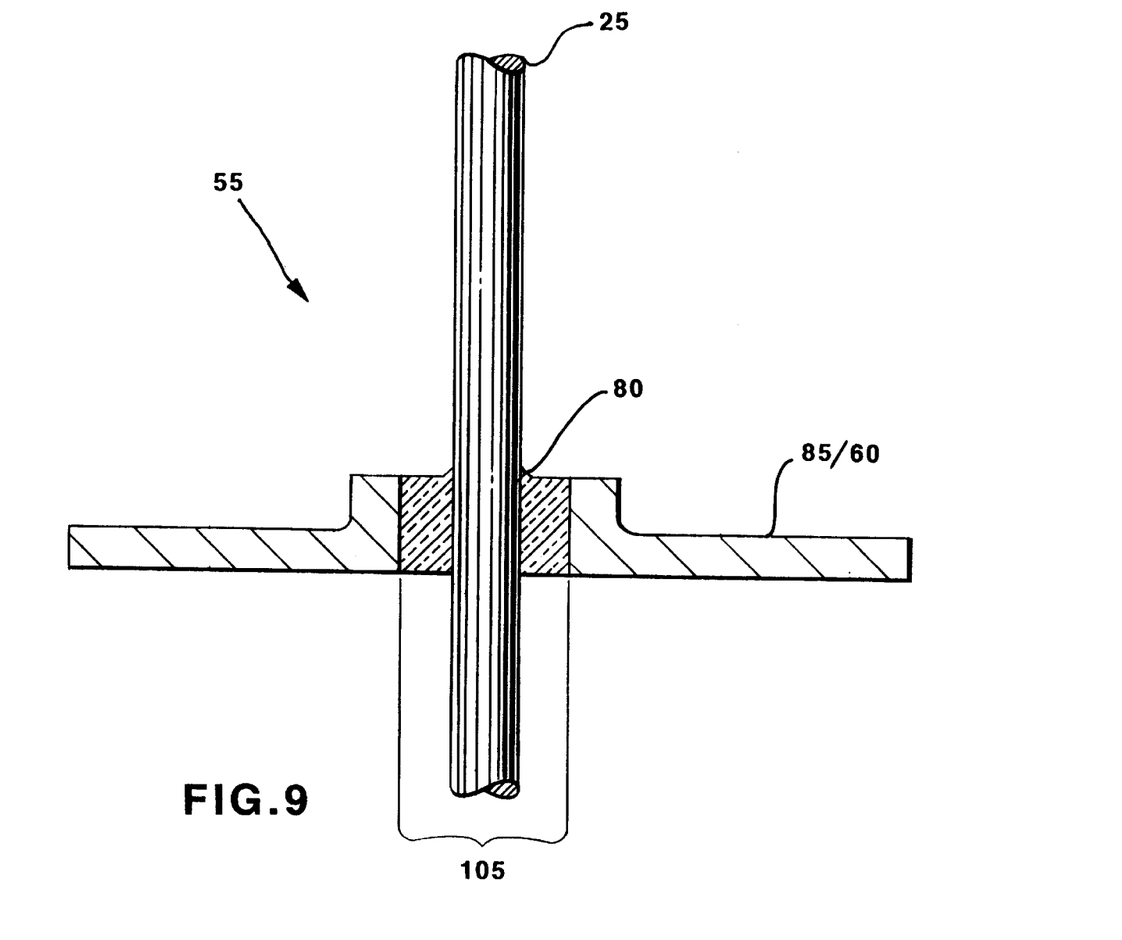
FIG. 9 shows a cross-sectional view of one embodiment of a glass-to-metal battery feedthrough of the present invention.

FIG. 9 shows a cross-sectional view of one embodiment of a glass-to-metal battery feedthrough of the present invention. In FIG. 9, feedthrough 55 is affixed in sealing engagement to battery case 85 or container 60, most preferably by using conventional glass sealing techniques to place and seal centerless ground pin 25 directly in aperture or opening 105 in cover 85 or container 60.

Figure 10:
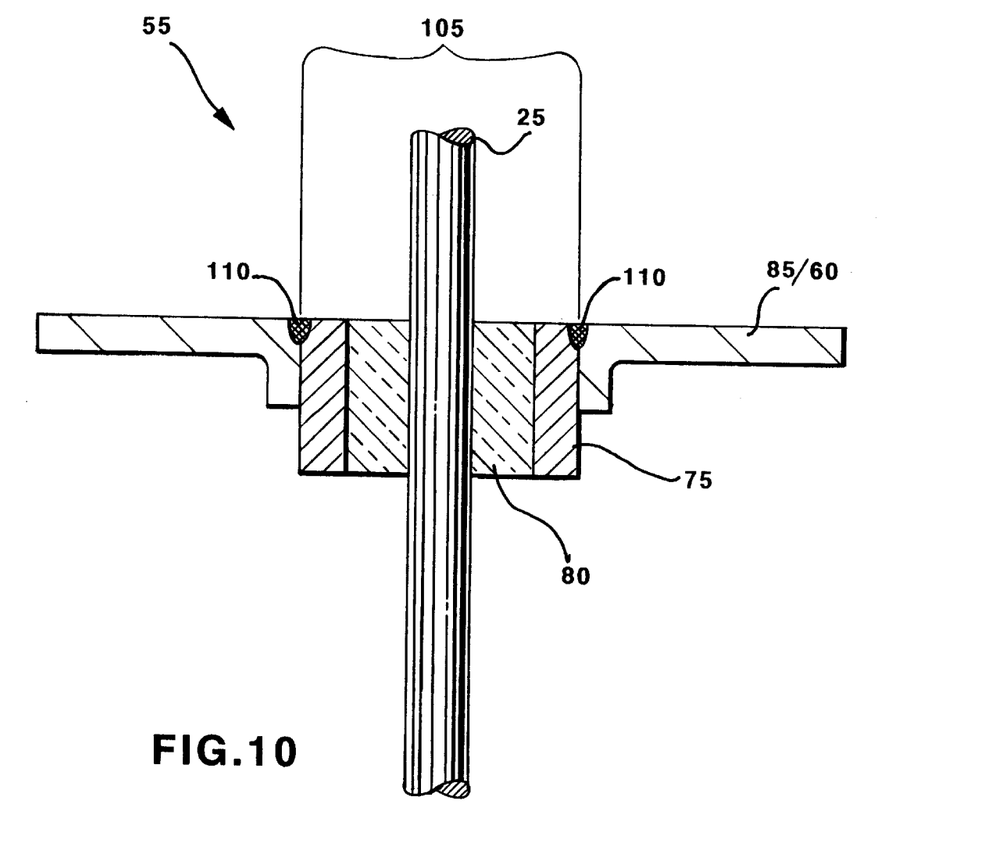
FIG. 10 shows a cross-sectional view of another embodiment of a glass-to-metal battery feedthrough of the present invention.

FIG. 10 shows a cross-sectional view of another embodiment of a glass-to-metal battery feedthrough of the present invention. In FIG. 10, ferrule 75 is welded in aperture or opening 105 by welds 110. Ferrule 75 and centerless ground pin 25 are affixed by sealing glass 80 using conventional sealing techniques.

Figure 11:
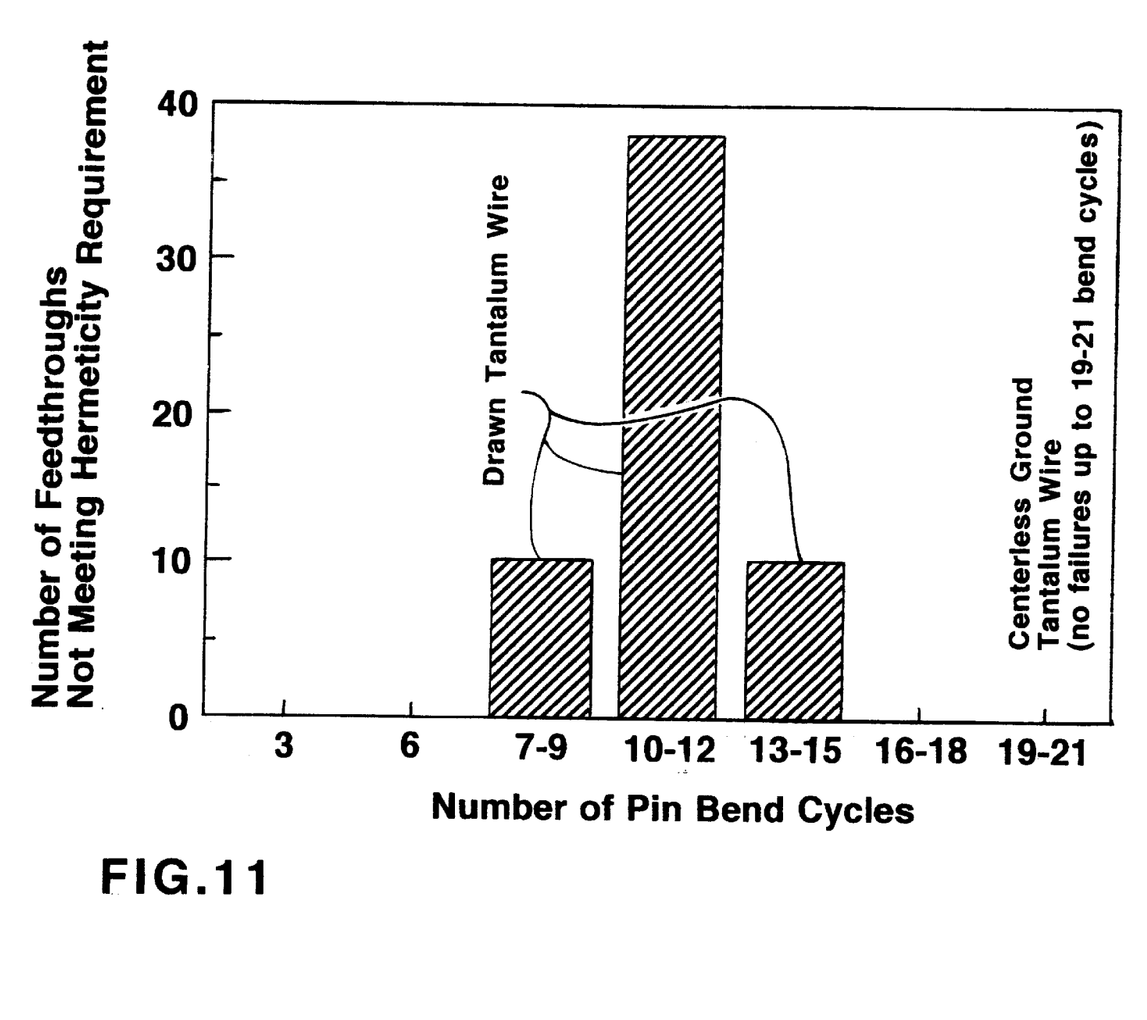
FIG. 11 shows comparative hermeticity test results obtained with feedthroughs of the prior art and feedthroughs of the present invention having centerless ground pins therein.

FIG. 11 shows comparative hermeticity test results obtained with feedthroughs of the prior art and feedthroughs of the present invention having centerless ground pins therein. FIG. 11 shows reliability differences measured between feedthroughs incorporating conventional drawn pins and those incorporating centerless ground pins. Note particularly the differences in the number of tensile-fatigue cycles sustained by feedthroughs without hermetic loss. Feedthroughs incorporating conventional drawn tantalum wire containing longitudinal anomalies of varying depths responded repeated cycles of mechanical stressing by beginning to lose hermeticity at 7–9 tensile-fatigue cycles. Hermeticity losses in conventional drawn wire accelerated thereafter as the number of tensile-fatigue cycles increased. By comparison, feedthroughs incorporating centerless ground tantalum pins maintained a predetermined, specified helium leak rate after completing 19–21 tensile-fatigue cycles. In fact, no tested centerless ground pins failed hermeticity requirements.

Those of ordinary skill will now appreciate that the method and device of the present invention are not limited to feedthroughs for implantable medical devices, but extend to methods and corresponding devices for stents and IPG electrical stimulation and sensing lead wires.

Additionally, although only a few exemplary embodiments of the present invention have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

The scope of the present invention is not limited to pacing, monitoring or sensing applications, but extends to defibrillation, neurological cardiac mapping and other medical and medical device applications and methods. The scope of the present invention is not limited to applications where a human heart is sensed, monitored, paced, or defibrillated, but includes similar applications in other mammalians and mammalian organs.

The preceding specific embodiments are illustrative of the practice of the invention. It is to be understood, therefore, that other expedients known to those skilled in the art or disclosed herein, may be employed without departing from the invention or the scope of the appended claims.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All patents or printed publications disclosed hereinabove are hereby incorporated by reference herein into the specification hereof, each in its respective entirety.

We claim:

1. A method of making a pin for a feedthrough in an implantable medical device, comprising of the steps of:

(a) selecting over-size medical grade wire;

(b) straightening the wire by passing the wire through at least one rotating die;

(c) cutting the wire to form a wire of desired length;

(d) centerless grinding the wire of desired length to remove at least one of an anomaly and a defect from the surface thereof, and (e) cutting the wire to form a pin having a final length suitable for use in the feedthrough, the pin having first and second ends.

2. The method of claim 1, further comprising the step of deburring at least one of the first and second ends of the pin.

3. The method of claim 1, further comprising the step of providing an abrasive wheel for the centerless grinding step.

4. The method of claim 1, further comprising the step of providing a suitable coolant for cooling the abrasive wheel during the centerless grinding step.

5. The method of claim 1, further comprising the step of providing at least one of an aluminum oxide abrasive wheel, cerium oxide abrasive wheel, boron nitride abrasive wheel, silicon carbide abrasive wheel, and diamond abrasive wheel for the centerless grinding step.

6. The method of claim 1, wherein the wire selecting step further comprises providing at least one of platinum wire, molybdenum wire, tantalum wire, titanium wire, niobium wire, stainless steel wire, aluminum wire, aluminum alloy wire, and wires formed of alloys, mixtures or combinations thereof.

* * * * *